(12) United States Patent
Takahashi et al.

(10) Patent No.: US 8,604,154 B2
(45) Date of Patent: Dec. 10, 2013

(54) CARBODIIMIDE COMPOUND, CARBODIIMIDE COMPOSITION AND AQUEOUS COATING COMPOSITION

(75) Inventors: Ikuo Takahashi, Chiba (JP); Kenichi Yanagisawa, Chiba (JP); Noriko Osuga, Chiba (JP)

(73) Assignee: Nisshinbo Holdings Inc., Tokyo (JP)

( * ) Notice: Subject to any disclaimer, the term of this patent is extended or adjusted under 35 U.S.C. 154(b) by 471 days.

(21) Appl. No.: 12/934,567

(22) PCT Filed: Mar. 17, 2009

(86) PCT No.: PCT/JP2009/055189
§ 371 (c)(1),
(2), (4) Date: Sep. 24, 2010

(87) PCT Pub. No.: WO2009/119389
PCT Pub. Date: Oct. 1, 2009

(65) Prior Publication Data
US 2011/0021679 A1   Jan. 27, 2011

(30) Foreign Application Priority Data
Mar. 27, 2008 (JP) .................................. 2008-084630

(51) Int. Cl.
*C08G 73/00* (2006.01)

(52) U.S. Cl.
USPC ............. 528/170; 528/61; 524/800; 524/901; 524/802; 524/839

(58) Field of Classification Search
USPC ............. 524/800, 801, 802, 839; 528/61, 170
See application file for complete search history.

(56) References Cited

U.S. PATENT DOCUMENTS

| | | | |
|---|---|---|---|
| 3,867,181 A * | 2/1975 | Vizurraga | 428/375 |
| 4,071,503 A * | 1/1978 | Thomas et al. | 525/440.02 |
| 5,108,653 A * | 4/1992 | Taylor | 516/71 |
| 5,117,059 A * | 5/1992 | Tylor | 564/252 |
| 5,693,736 A * | 12/1997 | Zoeller et al. | 528/44 |
| 5,728,432 A * | 3/1998 | Imashiro et al. | 427/389.8 |
| 5,859,166 A | 1/1999 | Sasaki et al. | |
| 6,121,406 A | 9/2000 | Imashiro et al. | |
| 6,124,398 A * | 9/2000 | Imashiro et al. | 525/61 |
| 6,184,410 B1 * | 2/2001 | Bollmann et al. | 560/26 |
| 6,329,491 B1 * | 12/2001 | Mormile et al. | 528/49 |
| 6,492,484 B2 * | 12/2002 | Misumi et al. | 528/170 |
| 6,599,975 B1 * | 7/2003 | Licht et al. | 524/591 |
| 6,730,807 B1 * | 5/2004 | Haberle et al. | 562/439 |
| 7,049,001 B2 * | 5/2006 | Haberle et al. | 428/423.1 |
| 7,919,149 B2 * | 4/2011 | Sato et al. | 427/407.1 |
| 2001/0037010 A1 * | 11/2001 | Tebbe et al. | 528/170 |
| 2002/0086162 A1 | 7/2002 | Masuda et al. | |
| 2003/0088030 A1 * | 5/2003 | Haberle et al. | 525/326.6 |
| 2005/0085616 A1 | 4/2005 | Licht et al. | |
| 2006/0194939 A1 * | 8/2006 | Licht et al. | 528/61 |
| 2009/0171016 A1 * | 7/2009 | Sato et al. | 524/608 |
| 2009/0246393 A1 * | 10/2009 | Ambrose et al. | 427/386 |
| 2011/0070374 A1 * | 3/2011 | Ambrose et al. | 427/385.5 |
| 2012/0264968 A1 * | 10/2012 | Yanagisawa et al. | 560/159 |

FOREIGN PATENT DOCUMENTS

| | | |
|---|---|---|
| JP | 10-60272 A | 3/1998 |
| JP | 2000-7642 A | 1/2000 |
| JP | 2000-154228 A | 6/2000 |
| JP | 2000-313825 A | 11/2000 |
| JP | 2000-319351 A | 11/2000 |
| JP | 2001-11151 A | 1/2001 |
| JP | 2003-306476 A | 10/2003 |
| JP | 2008-521758 A | 7/2005 |
| JP | 2008-63442 A | 3/2008 |
| WO | WO 2007/089142 A1 | 8/2007 |

OTHER PUBLICATIONS

EIC structure search 12934567-429542-EICSEARCH.pdf; Jul. 2013.*
Extended European Search Report dated Jan. 30, 2013, for European Patent Application No. 09725074.

* cited by examiner

*Primary Examiner* — Peter F Godenschwager
*Assistant Examiner* — Jane L Stanley
(74) *Attorney, Agent, or Firm* — Birch, Stewart, Kolasch & Birch, LLP

(57) ABSTRACT

A water-soluble or water-dispersible carbodiimide compound is hydrophilicized by incorporating methyl glycolate or methyl lactate, which serves a moiety similar to the moiety which aqueous urethane resin, aqueous acrylic resin, or the like possesses, into an end of a starting carbodiimide compound. The invention provides a carbodiimide compound and a carbodiimide composition, which, when added as a crosslinking agent to aqueous resin, can enhance water resistance, solvent resistance, and adhesion of the resin, while maintaining the conventionally attained pot life, and an aqueous coating composition containing the carbodiimide compound or composition.

10 Claims, No Drawings

CARBODIIMIDE COMPOUND, CARBODIIMIDE COMPOSITION AND AQUEOUS COATING COMPOSITION

TECHNICAL FIELD

The present invention relates to a carbodiimide compound, to a carbodiimide composition, and to an aqueous coating composition. More particularly, the invention relates to a carbodiimide compound, to a carbodiimide composition, and to an aqueous coating composition containing the compound or composition, each of which is useful in improving water resistance, solvent resistance, and adhesion of a formed coating film.

BACKGROUND ART

Aqueous resin, which has solubility or dispersibility in water, finds a variety of uses, including coating, ink, a fiber-treatment agent, an adhesive, and a coating agent.

In recent years, there has arisen a sharp demand for such water-soluble or water-dispersible aqueous coating materials employing an aqueous medium, since they do not cause environmental pollution or fire, and coaters (e.g., brush, roller, and spray gun) and remaining coating materials can be readily cleaned by use of water.

For producing aqueous resin having solubility or dispersibility in water, a carboxylic group is generally incorporated into the resin. However, carboxylic groups remaining in the formed coating film cause hydrolysis of the resin, and in some cases, the strength, durability, and appearance of the coating film are impaired.

In order to enhance physical properties (e.g., strength, durability, and appearance) of coating film formed from such an aqueous resin, external cross-linking agents such as an aqueous melamine resin, an aziridine compound, and a water-dispersed isocyanate compound, which can form a cross-linking structure through reaction with the aforementioned carboxylic group, are generally employed.

However, these external cross-linking agents may be difficult to handle due to problems in toxicity, reactivity, etc. More specifically, cross-linking reaction involving the cross-linking agent of the above type proceeds with transformation of carboxylic groups. That is, when the number of the carboxylic groups decreases, the strength, durability, appearance, etc. of the coating film is enhanced. However, unreacted portions of the cross-linking agent remaining in the coating film may cause toxicity. When unreacted carboxylic groups remain in the coating film, water resistance and durability of the coating film are impaired. Thus, incomplete reaction of the cross-linking agent and the carboxylic groups in the aqueous resin results in various problems.

Recently, carbodiimide compounds have become of interest, since they can resolve the problem of toxicity. For example, Patent Document 1 discloses aqueous dicyclohexylmethanecarbodiimide, which exhibits excellent reactivity and storage stability and which can be readily handled as a cross-linking agent for forming aqueous resin.

The disclosed aqueous dicyclohexylmethanecarbodiimide has no toxicity and a sufficiently long pot life.
Patent Document 1: Japanese Patent Application Laid-Open (kokai) No. 2000-7462

DISCLOSURE OF THE INVENTION

Problems to be Solved by the Invention

However, the present inventors have noted drawbacks of the aforementioned aqueous dicyclohexylmethanecarbodiimide. Specifically, even when the aqueous dicyclohexylmethanecarbodiimide is used, some resins may fail to attain sufficient water resistance and solvent resistance. When cross-linking density is increased in order to enhance water resistance and solvent resistance, the pot life of the composition is problematically shortened.

Thus, an object of the present invention is to provide a carbodiimide compound and a carbodiimide composition, which, when added as a cross-linking agent to aqueous resin, can enhance water resistance, solvent resistance, and adhesion of the resin, while maintaining the conventionally attained pot life. Another object is to provide an aqueous coating composition containing the carbodiimide compound or composition.

Means for Solving the Problems

In order to attain the object, the present inventors have conducted extensive studies, and have found that the aforementioned object can be attained by a water-soluble or water-dispersible carbodiimide compound which has been hydrophilicized by incorporating methyl glycolate or methyl lactate, which serves a moiety similar to the moiety possessed by aqueous urethane resin, aqueous acrylic resin, or the like, into an end of a starting carbodiimide compound. The present invention has been accomplished on the basis of this finding.

Accordingly, the present invention provides the following.
1. A carbodiimide compound represented by formula (1):

[F1]

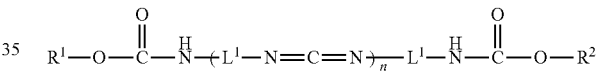
(1)

(wherein $R^1$ represents a group represented by formula (a):

[F2]

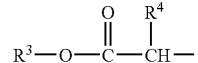
(a)

(wherein $R^3$ represents a C1 to C3 alkyl group; and $R^4$ represents a hydrogen atom or a C1 to C3 alkyl group); $R^2$ represents a group represented by formula (a) or (b):

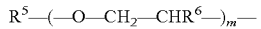
(b)

(wherein $R^5$ represents a C1 to C4 alkyl group, $R^6$ represents a hydrogen atom or a methyl group; and m is an integer of 4 to 30); n is an integer of 1 to 15; $L^1$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^1$s may be identical to or different from one another).

2. A carbodiimide compound represented by formula (1-a):

(1-a)

[F3]

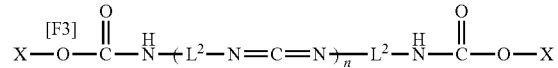

(wherein X represents a group represented by formula (a):

[F4]

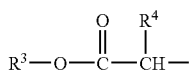
(a)

(wherein $R^3$ represents a C1 to C3 alkyl group; and $R^4$ represents a hydrogen atom or a C1 to C3 alkyl group), and a plurality of Xs may be identical to or different from one another; n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another).

3. A carbodiimide compound represented by formula (1-b):

[F5]

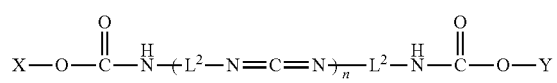
(1-b)

(wherein X represents a group represented by formula (a):

[F6]

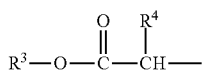
(a)

(wherein $R^3$ represents a C1 to C3 alkyl group; and $R^4$ represents a hydrogen atom or a C1 to C3 alkyl group); Y represents a group represented by formula (b):

$R^5$—(—O—CH$_2$—CHR$^6$—)$_m$— (b)

(wherein $R^5$ represents a C1 to C4 alkyl group, $R^6$ represents a hydrogen atom or a methyl group; and m is an integer of 4 to 30); n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another).

4. An aqueous coating composition comprising a carbodiimide compound as recited in any one of 1 to 3 above, and a cross-linkable aqueous resin.

5. A carbodiimide composition comprising a carbodiimide compound represented by formula (1-a); a carbodiimide compound represented by formula (1-b); and a carbodiimide compound represented by formula (2):

[F7]

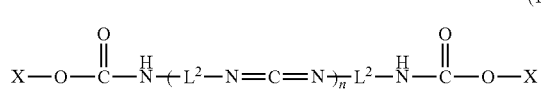
(1-a)

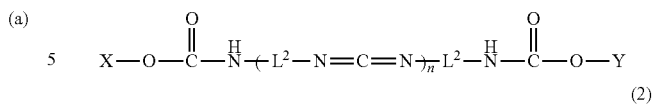
(1-b)

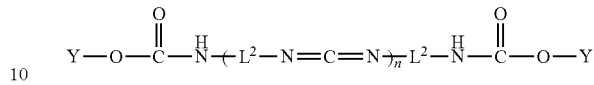
(2)

(wherein X represents a group represented by formula (a):

[F8]

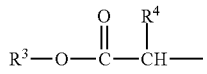
(a)

(wherein $R^3$ represents a C1 to C3 alkyl group; and $R^4$ represents a hydrogen atom or a C1 to C3 alkyl group), and a plurality of Xs may be identical to or different from one another; Y represents a group represented by formula (b):

$R^5$—(—O—(CH$_2$—CHR$^6$—)$_m$— (b)

(wherein $R^5$ represents a C1 to C4 alkyl group, $R^6$ represents a hydrogen atom or a methyl group; and m is an integer of 4 to 30), and a plurality of Ys may be identical to or different from one another; n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another).

6. An aqueous coating composition comprising a carbodiimide composition as recited in 5 above, and a cross-linkable aqueous resin.

Effects of the Invention

Aqueous coating compositions containing the carbodiimide compound or the carbodiimide composition of the present invention exhibit excellent water resistance, solvent resistance, adhesion, and appearance, while maintaining the conventionally attained pot life.

BEST MODES FOR CARRYING OUT THE INVENTION

The present invention will next be described in more detail.

The carbodiimide compound of the present invention has a specific hydrophilic segment at an end thereof. Thus, it is water-soluble or water-dispersible and can be particularly suitably employed as a cross-linking agent for aqueous resin.

The carbodiimide compound of the present invention is represented by formula (1):

[F9]

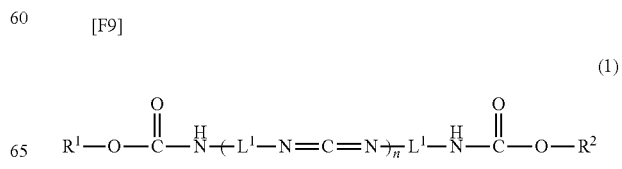
(1)

(wherein $R^1$ represents a group represented by formula (a):

[F10]

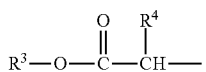
(a)

(wherein $R^3$ represents a C1 to C3 alkyl group; and $R^4$ represents a hydrogen atom or a C1 to C3 alkyl group); $R^2$ represents a group represented by formula (a) or (b):

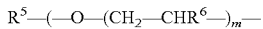
(b)

(wherein $R^5$ represents a C1 to C4 alkyl group, $R^6$ represents a hydrogen atom or a methyl group; and m is an integer of 4 to 30); n is an integer of 1 to 15; $L^1$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^1$s may be identical to or different from one another).

The carbodiimide compound of the present invention is preferably a compound represented by formula (1-a), since the compound improves water resistance, solvent resistance, and adhesion of the resin composition to which the compound has been added as a cross-linking agent. Also, the carbodiimide compound of the present invention is preferably a compound represented by formula (1-b), since the carbodiimide compound has high water solubility which is readily adaptable to a completely aqueous medium.

[F11]

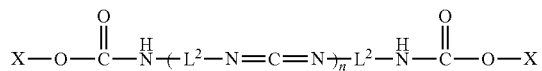
(1-a)

(wherein X represents a group represented by formula (a), and a plurality of Xs may be identical to or different from one another; n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another).

[F12]

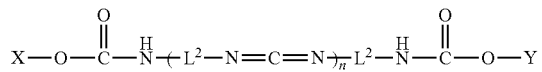
(1-b)

(wherein X represents a group represented by formula (a); Y represents a group represented by formula (b); n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another).

The carbodiimide composition of the present invention contains a carbodiimide compound represented by formula (1-a); a carbodiimide compound represented by formula (1-b); and a carbodiimide compound represented by formula (2):

[F13]

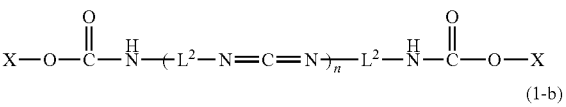
(1-a)

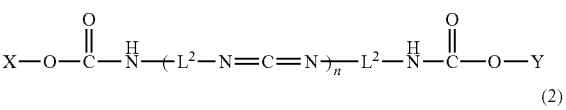
(1-b)

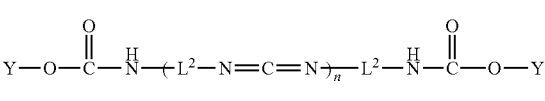
(2)

(wherein X represents a group represented by formula (a); Y represents a group represented by formula (b); n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another).

In the aforementioned formulas (1), (1-a), (1-b), and (2), n is an integer of 2 to 15, preferably 2 to 10. When the conditions of n are satisfied, the poly-carbodiimide compound is soluble in an aqueous medium or has an excellent dispersibility in an aqueous medium.

The divalent aliphatic hydrocarbon group, divalent alicyclic hydrocarbon group, divalent aromatic hydrocarbon group, or divalent heterocyclic group represented by $L^1$ or $L^2$ may have a substituent. The substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or an aromatic heterocyclic group. The substituent is more preferably an alkyl group, an aryl group, an alkoxy group, an aryloxy group, a halogen atom, or a cyano group. The substituent is still more preferably an alkyl group, an aryl group, an alkoxy group, or an aryloxy group, with an alkyl group, an aryl group, and an alkoxy group being particularly preferred.

Specific examples of the C1 to C18 divalent aliphatic hydrocarbon group in the aforementioned formulas (1), (1-a), (1-b), and (2) include divalent groups derived from methyl, ethyl, propyl, isopropyl, n-butyl, sec-butyl, tert-butyl, pentyl, hexyl, heptyl, octyl, stearyl, 2-phenylisopropyl, benzyl, α-phenoxybenzyl, α,α-dimethylbenzyl, α,α-methylphenylbenzyl, α,α-ditrifluoromethylbenzyl, and α-benzyloxybenzyl.

Specific examples of the C3 to C13 divalent alicyclic hydrocarbon group in the aforementioned formulas (1), (1-a), (1-b), and (2) include divalent groups derived from cyclopropyl, cyclobutyl, cyclopentyl, cyclohexyl, cycloheptyl, cyclooctyl, cyclononyl, bicycloheptyl, bicyclooctyl, tricycloheptyl, and adamantyl; and a divalent group derived from dicyclohexylmethane. Among them, divalent groups derived from cyclopentyl, cyclohexyl, cycloheptyl, bicycloheptyl, bicyclooctyl, and adamantyl, and a divalent group derived from dicyclohexylmethane are preferred.

Specific examples of the C6 to C14 divalent aromatic hydrocarbon group in the aforementioned formulas (1), (1-a), (1-b), and (2) include phenylene, naphthylene, biphenylene, anthranylene, perylenylene, and pyrenylene. Of these, phenylene, naphthylene, and biphenylene are preferred.

Specific examples of the C3 to C12 divalent heterocyclic group in the aforementioned formulas (1), (1-a), (1-b), and (2) include heterocyclic groups derived from imidazole, benzimidazole, pyrrole, furan, thiophene, benzothiophene, oxadiazoline, indoline, carbazole, pyridine, quinoline, isoquinoline, benzoquinone, pyralodine, imidazolidine, and piperidine.

Specific examples of the C1 to C3 alkyl group in the aforementioned formula (a) include methyl, ethyl, propyl, and isopropyl.

Specific examples of the C1 to C4 alkyl group in the aforementioned formula (b) include methyl, ethyl, propyl, isopropyl, n-butyl, sec-butyl, and tert-butyl.

The carbodiimide compound of the present invention may be produced through, for example, condensing an organic diisocyanate compound concomitant with removal of carbon dioxide to thereby synthesize an isocyanate-terminated polycarbodiimide compound, and reacting this product with a hydrophilic organic compound A having a functional group reactive with an isocyanate group and represented by formula (A):

[F14]

(A)

(wherein $R^3$ represents a C1 to C3 alkyl group; and $R^4$ represents a hydrogen atom or a C1 to C3 alkyl group). Alternatively, the carbodiimide composition of the present invention containing a carbodiimide compound may be produced through reacting the isocyanate-terminated polycarbodiimide compound with a mixture of the hydrophilic organic compound A represented by formula (A) and a hydrophilic organic compound B represented by formula (B):

(B)

(wherein $R^5$ represents a C1 to C4 alkyl group; $R^6$ represents a hydrogen atom or a methyl group; and m is an integer of 4 to 30), to thereby end-cap the end isocyanate group with a hydrophilic segment.

Specific examples of the C1 to C3 alkyl group in the aforementioned formula (A) include methyl, ethyl, propyl, and isopropyl.

Specific examples of the C1 to C4 alkyl group in the aforementioned formula (B) include methyl, ethyl, propyl, isopropyl, n-butyl, s-butyl, isobutyl, and tert-butyl.

The aforementioned hydrophilic organic compounds A represented by formula (A) or hydrophilic organic compounds B represented by formula (B) may be used singly or in combination of two or more species.

The aforementioned hydrophilic organic compound A represented by formula (A) is preferably methyl glycolate or methyl lactate, and the aforementioned hydrophilic organic compound B represented by formula (B) is preferably polyethylene glycol monomethyl ether.

Examples of the organic diisocyanate compound serving as the raw material of the isocyanate-terminated carbodiimide compound include aromatic diisocyanate compounds, aliphatic diisocyanate compounds, alicyclic diisocyanate compounds, heterocyclic diisocyanate compounds, and mixtures thereof. Specific examples include 1,5-naphthylene diisocyanate, 4,4'-diphenylmethane diisocyanate, 4,4'-diphenyldimethylmethane diisocyanate, 1,3-phenylene diisocyanate, 1,4-phenylene diisocyanate, 2,4-tolylene diisocyanate, 2,6-tolylene diisocyanate, a mixture of 2,4-tolylene diisocyanate and 2,6-tolylene diisocyanate, hexamethylene diisocyanate, cyclohexane-1,4-diisocyanate, xylylene diisocyanate, isophorone diisocyanate, dicyclohexylmethane 4,4'-diisocyanate, methylcyclohexane diisocyanate, tetramethylxylylene diisocyanate, and 2,5(2,6)-bis(isocyanatomethyl)bicyclo[2.2.1]heptane.

Condensation of an organic diisocyanate compound concomitant with removal of carbon dioxide proceeds in the presence of a carbodiimidation catalyst. Examples of the catalyst which may be used in the invention include 1-phenyl-2-phospholene 1-oxide, 3-methyl-2-phospholene 1-oxide, 1-ethyl-2-phospholene 1-oxide, 3-methyl-1-phenyl-2-phospholene 1-oxide, and phospholene oxides of 3-phospholene isomers. Of these, 3-methyl-1-phenyl-2-phospholene 1-oxide is preferred, from the viewpoint of reactivity. The aforementioned catalyst may be used in a catalytic amount.

The condensation reaction of the organic diisocyanate compound is generally performed at about 80 to about 200° C.

Addition of a hydrophilic segment to the isocyanate-terminated carbodiimide compound through reaction with the hydrophilic organic compound A or a mixture of the hydrophilic organic compounds A and B is generally performed at 60 to 180° C., preferably 100 to 160° C.

Among the thus-produced carbodiimide compounds falling within the scope of the present invention, aliphatic carbodiimide compounds are preferred as cross-linking agents, and dicyclohexylmethanecarbodiimide and tetramethylxylylenecarbodiimide are more preferred, with dicyclohexylmethanecarbodiimide being particularly preferred, from the viewpoints of reactivity and storage stability. Dicyclohexylmethanecarbodiimide may be produced through condensing 4,4'-dicyclohexylmethane diisocyanate in the presence of the aforementioned carbodiimidation catalyst to thereby produce isocyanate-terminated dicyclohexylmethanecarbodiimide, and reacting this product with the aforementioned hydrophilic organic compound A or with a mixture of the hydrophilic organic compounds A and B to thereby end-cap the terminal isocyanate group with a hydrophilic segment.

The hydrophilic organic compound A represented by formula (A) reacts with the isocyanate group of the isocyanate-terminated carbodiimide compound to form a group represented by formula (a), and the hydrophilic organic compound B represented by formula (B) reacts with the isocyanate group of the isocyanate-terminated carbodiimide compound to form a group represented by formula (b).

In the carbodiimide composition of the present invention, the mole ratio of group represented by formula (a) to group represented by formula (b) is preferably 1:10 to 30:1 in terms of well-balanced cross-linking performance and solubility in water when the composition is used as a cross-linking agent. The ratio is more preferably 1:1 to 15:1.

The present invention also provides an aqueous coating composition containing the carbodiimide compound of the present invention and a cross-linkable aqueous resin, and an aqueous coating composition containing the carbodiimide composition of the present invention and a cross-linkable aqueous resin.

In the aqueous coating composition of the present invention, the compositional proportions among the ingredients may be adjusted as desired. However, in consideration of the balance in the physical properties of the formed coating film and production cost, the carbodiimide compound or carbodiimide composition is preferably used in an amount of 0.5 to 15 parts by mass, particularly preferably 1 to 10 parts by mass, with respect to 100 parts by mass of the aqueous resin.

No particular limitation is imposed on the resin concentration of the aqueous solution or water dispersion containing the aqueous resin. However, from the viewpoints of the coatability of the produced aqueous coating composition, the drying performance of the coated layer, etc., the concentration is preferably about 15 to about 50 mass %, more preferably about 20 to about 40 mass %.

The aqueous coating composition of the present invention is a dispersion of a coating composition in an aqueous medium. No particular limitation is imposed on the aqueous medium, and water, a mixture of water and another solvent, etc. may be used. No particular limitation is imposed on the solvent used with water, so long as the solvent has compatibility with water. Examples of the solvent include hydrocarbons such as xylene and toluene; alcohols such as methyl alcohol, n-butyl alcohol, isopropyl alcohol, 2-ethylhexyl alcohol, ethylene glycol, propylene glycol, 2-(2-n-butoxyethoxy)ethanol; ethers such as ethylene glycol monoethyl ether, ethylene glycol monobutyl ether, ethylene glycol monohexyl ether, propylene glycol monoethyl ether, 3-methyl-3-methoxybutanol, diethylene glycol monoethyl ether, and diethylene glycol monobutyl ether; ketones such as methyl isobutyl ketone, cyclohexanone, isophorone, and acetylacetone; esters such as ethylene glycol monoethyl ether acetate, and ethylene glycol monobutyl ether acetate; and mixtures thereof.

The aqueous medium is preferably a completely aqueous system (i.e., sole water) from the viewpoint of the environment.

If required, the aqueous coating composition of the present invention may further contain a variety of appropriate additives in accordance with use thereof, and examples of such additives include a pigment, a filler, a leveling agent, a surfactant, a dispersant, a plasticizer, a UV-absorber, and an antioxidant.

In the case where the aqueous coating composition of the present invention contains the carbodiimide compound of the present invention represented by formula (1-a), the coating composition can be made water-soluble or water-dispersible by incorporating a surfactant, a dispersant, etc. thereinto, or by incorporating another carbodiimide compound having an end hydrophilic organic compound moiety thereinto.

Through applying the aqueous coating composition of the present invention onto a substrate of interest, a coating layer can be formed, and a coating film can be yielded from the coating layer.

No particular limitation is imposed on the coating method, and conventionally known methods may be appropriately employed. Examples of the employable coating method include brush coating, padding, spraying, hot-spraying, airless-spraying, roller coating, curtain flow coating, flow coating, dip coating, and knife-edge coating.

After formation of the coating layer, the layer may be subjected to curing treatment in order to accelerate curing. The curing is generally performed by heating to accelerate cross-linking reaction to form a coating film. No particular limitation is imposed on the heating method, and heating may be performed by means of an electric furnace, a hot blow furnace, an infrared furnace, a high-frequency furnace, etc.

EXAMPLES

The present invention will next be described in detail by way of the Synthesis Examples, Examples, and Comparative Examples, which should not be construed as limiting the invention thereto.

In the following Examples, analyses of the products were carried out through the following methods.
(IR)
By means of FTIR-8200PC (Shimadzu Corporation).
(GPC)
RI detector: RID-6A (Shimadzu Corporation)
Column: KF-806, KF-804L, and KF-804L
Developing solvent: THF 1 mL/min.
Polystyrene standard
(NCO %)
By means of Hiranuma Automated Titrator COM-900 (Hiranuma Sangyo Co., Ltd.) and Tit-station K-900 (Hiranuma Sangyo Co., Ltd.). A dibutylamine/toluene solution having a known concentration was added, and potentiometric titration was performed by use of aqueous hydrochloric acid.

Synthesis Example 1

Polymerization to Produce Isocyanate-terminated Carbodiimide

To a reactor (capacity: 3,000 mL) equipped with a reflux tube and a stirrer, 4,4'-dicyclohexylmethane diisocyanate (1,572 g) and a carbodiimidation catalyst (3-methyl-1-phenyl-2-phospholene 1-oxide) (7.86 g) were added. The mixture was stirred at 185° C. for 10 hours under a stream of nitrogen, to thereby yield isocyanate-terminated 4,4'-dicyclohexylmethanecarbodiimide (polymerization degree: 3). Through infrared absorption (IR) spectrometry, a peak attributed to a carbodiimide group near 2,150 cm$^{-1}$ was detected. The NCO % was found to be 9.16%.

Synthesis Example 2

End-capping with Polyethylene Glycol Monomethyl Ether and Methyl Lactate

The isocyanate-terminated 4,4'-dicyclohexylmethanecarbodiimide (polymerization degree: 3) produced in Synthesis Example 1 (51.8 g) was melted at 120° C., and polyethylene glycol monomethyl ether (average molecular weight: 400) (13.6 g) and methyl lactate (8.2 g) were added to the melt. The mixture was heated to 150° C. and allowed to react for five hours under stirring. Disappearance of the peak attributed to an isocyanate group 2,200 to 2,300 cm$^{-1}$ was confirmed through infrared absorption (IR) spectrometry, and the mixture was cooled to about 80° C. Water was added to the cooled mixture, to thereby yield a pale yellow, transparent carbodiimide solution having a solid content of 40 mass %. Through GPC measurement, the average molecular weight (polystyrene standard) was found to be 1,500.

Synthesis Example 3

End-capping with Polyethylene Glycol Monomethyl Ether and Methyl Glycolate

The isocyanate-terminated 4,4'-dicyclohexylmethanecarbodiimide (polymerization degree: 3) produced in Synthesis Example 1 (51.8 g) was melted at 120° C., and polyethylene glycol monomethyl ether (average molecular weight: 400) (13.6 g) and methyl glycolate (7.1 g) were added to the melt. The mixture was heated to 150° C. and allowed to react for five hours under stirring. Disappearance of the peak attributed to an isocyanate group 2,200 to 2,300 cm$^{-1}$ was confirmed through infrared absorption (IR) spectrometry, and the mixture was cooled to about 80° C. Water was added to the cooled mixture, to thereby yield a pale yellow, transparent carbodiimide solution having a solid content of 40 mass %. Through GPC measurement, the average molecular weight (polystyrene standard) was found to be 1,500.

Synthesis Example 4

End-capping with Methyl Lactate

The isocyanate-terminated 4,4'-dicyclohexylmethanecarbodiimide (polymerization degree: 3) produced in Synthesis Example 1 (51.8 g) was melted at 120° C., and methyl lactate (12.7 g) was added to the melt. The mixture was heated to 150° C. and allowed to react for five hours under stirring. Disappearance of the peak attributed to an isocyanate group 2,200 to 2,300 cm$^{-1}$ was confirmed through infrared absorption (IR) spectrometry. Through GPC measurement, the average molecular weight (polystyrene standard) was found to be 1,300. The mixture was cooled to about 80° C., and 2-(2-n-butoxyethoxy)ethanol was added to the cooled mixture, to thereby yield a pale yellow, transparent carbodiimide solution having a solid content of 40 mass %.

Synthesis Example 5

End-capping with Methyl Glycolate

The isocyanate-terminated 4,4'-dicyclohexylmethanecarbodiimide (polymerization degree: 3) produced in Synthesis Example 1 (51.8 g) was melted at 120° C., and methyl glycolate (11.0 g) was added to the melt. The mixture was heated to 150° C. and allowed to react for five hours under stirring. Disappearance of the peak attributed to an isocyanate group 2,200 to 2,300 cm$^{-1}$ was confirmed through infrared absorption (IR) spectrometry. Through GPC measurement, the average molecular weight (polystyrene standard) was found to be 1,300. The mixture was cooled to about 80° C., and 2-(2-n-butoxyethoxy)ethanol was added to the cooled mixture, to thereby yield a pale yellow, transparent carbodiimide solution having a solid content of 40 mass %.

Synthesis Example 6

End-capping with Polyethylene Glycol Monomethyl Ether

The isocyanate-terminated 4,4'-dicyclohexylmethanecarbodiimide (polymerization degree: 3) produced in Synthesis Example 1 (51.8 g) was melted at 120° C., and polyethylene glycol monomethyl ether (average molecular weight: 380) (42.9 g) was added to the melt. The mixture was heated to 150° C. and allowed to react for five hours under stirring. Disappearance of the peak attributed to an isocyanate group 2,200 to 2,300 cm$^{-1}$ was confirmed through infrared absorption (IR) spectrometry. Through GPC measurement, the average molecular weight (polystyrene standard) was found to be 2,000. The mixture was cooled to about 80° C., and water was added to the cooled mixture, to thereby yield a pale yellow, transparent carbodiimide solution having a solid content of 40 mass %.

Synthesis Example 7

End-capping with Methanol

The isocyanate-terminated 4,4'-dicyclohexylmethanecarbodiimide (polymerization degree: 3) produced in Synthesis Example 1 (51.8 g) was melted at 120° C., and the melt was cooled to 65° C. Methanol (7.75 g) was added to the cooled product, and the mixture was allowed to react for eight hours under stirring. Disappearance of the peak attributed to an isocyanate group 2,200 to 2,300 cm$^{-1}$ was confirmed through infrared absorption (IR) spectrometry. Through GPC measurement, the average molecular weight (polystyrene standard) was found to be 1,000. 2-(2-n-Butoxyethoxy)ethanol was added to the cooled mixture, to thereby yield a pale yellow, transparent carbodiimide solution having a solid content of 40 mass %.

Example 1

Aqueous Coating Composition Containing Acrylic Resin

The carbodiimide solution produced in Synthesis Example 2 (2.6 g) was added to acrylic resin (Carboset 519, product of Noveon) (10 g), and the mixture was sufficiently stirred, to thereby prepare an aqueous coating composition.

The thus-prepared aqueous coating composition was cast on an aluminum plate (200 mm×100 mm×1 mm) to a coating thickness of 20 μm, to thereby form a coating film. Then, the film was cured at 100° C. for 10 minutes.

Example 2

Aqueous Coating Composition Containing Acrylic Resin

The procedure of Example 1 was repeated, except that the carbodiimide solution produced in Synthesis Example 3 was used instead of that produced in Synthesis Example 2, to thereby form a coating film.

Example 3

Aqueous Coating Composition Containing Acrylic Resin

The procedure of Example 1 was repeated, except that the carbodiimide solution produced in Synthesis Example 4 was used instead of that produced in Synthesis Example 2, to thereby form a coating film.

Example 4

Aqueous Coating Composition Containing Acrylic Resin

The procedure of Example 1 was repeated, except that the carbodiimide solution produced in Synthesis Example 5 was used instead of that produced in Synthesis Example 2, to thereby form a coating film.

Comparative Example 1

Aqueous Coating Composition Containing Acrylic Resin

The procedure of Example 1 was repeated, except that the carbodiimide solution produced in Synthesis Example 6 (3.4 g) was used instead of that produced in Synthesis Example 2, to thereby form a coating film.

Comparative Example 2

Aqueous Coating Composition Containing Acrylic Resin

The procedure of Example 1 was repeated, except that the carbodiimide solution produced in Synthesis Example 7 (2.6 g) was used instead of that produced in Synthesis Example 2, to thereby form a coating film.

Comparative Example 3

Aqueous Coating Composition Containing Acrylic Resin

The procedure of Example 1 was repeated, except that an acrylic resin (Carboset 519, product of Noveon) (10 g) was used without adding an carbodiimide solution, to thereby form a coating film.

Example 5

Aqueous Coating Composition Containing Polyurethane Resin

The carbodiimide solution produced in Synthesis Example 2 (2.0 g) was added to a polyurethane resin (U915, product of Alberdingk) (10 g), and the mixture was sufficiently stirred, to thereby prepare an aqueous coating composition. A coating film was formed from the composition in a manner similar to that of Example 1.

Example 6

Aqueous Coating Composition Containing Polyurethane Resin

The procedure of Example 5 was repeated, except that the carbodiimide solution produced in Synthesis Example 3 was used instead of that produced in Synthesis Example 2, to thereby form a coating film.

Example 7

Aqueous Coating Composition Containing Polyurethane Resin

The procedure of Example 5 was repeated, except that the carbodiimide solution produced in Synthesis Example 4 was used instead of that produced in Synthesis Example 2, to thereby form a coating film.

Example 8

Aqueous Coating Composition Containing Polyurethane Resin

The procedure of Example 5 was repeated, except that the carbodiimide solution produced in Synthesis Example 5 was used instead of that produced in Synthesis Example 2, to thereby form a coating film.

Comparative Example 4

Aqueous Coating Composition Containing Polyurethane Resin

The procedure of Example 5 was repeated, except that the carbodiimide solution produced in Synthesis Example 6 (2.6 g) was used instead of that produced in Synthesis Example 2, to thereby form a coating film.

Comparative Example 5

Aqueous Coating Composition Containing Polyurethane Resin

The procedure of Example 5 was repeated, except that the carbodiimide solution produced in Synthesis Example 7 (2.0 g) was used instead of that produced in Synthesis Example 2, to thereby form a coating film.

Comparative Example 6

Aqueous Coating Composition Containing Polyurethane Resin

The procedure of Example 5 was repeated, except that a polyurethane resin (U915, product of Alberdingk) (10 g) was used without adding an carbodiimide solution, to thereby form a coating film.

The thus-formed coating films were subjected to the rubbing test as described below. Table 1 shows the results.

(Rubbing Test)

Each coating film was subjected to double rubbing at a load of 900 g/cm$^2$ by means of a friction tester FR-1B (Suga Test Instruments Co., Ltd.) by use of methyl ethyl ketone (MEK) or ethanol as a solvent. The number of rubbing cycles until the coating film was peeled off was visually counted.

TABLE 1

|  | Solvent-resistant test (no. of friction) | |
| --- | --- | --- |
|  | MEK | ethanol |
| Ex. 1 | 37 | 61 |
| Ex. 2 | 40 | 75 |
| Ex. 3 | 35 | 60 |
| Ex. 4 | 42 | 74 |
| Comp. Ex. 1 | 4 | 30 |
| Comp. Ex. 2 | 10 | 32 |
| Comp. Ex. 3 | 3 | 3 |
| Ex. 5 | 200 | 75 |
| Ex. 6 | 200 | 83 |
| Ex. 7 | 200 | 73 |
| Ex. 8 | 200 | 85 |
| Comp. Ex. 4 | 48 | 36 |
| Comp. Ex. 5 | 52 | 44 |
| Comp. Ex. 6 | 7 | 10 |

As shown in Table 1, the coating films formed in Examples 1 to 8 exhibited excellent solvent resistance, as compared with the coating films produced by use of the same aqueous resins in Comparative Examples 1 to 6.

The thus-formed coating films were also subjected to the spot test as described in Table 2. Tables 3 and 4 show the results.

(Spot Test)

A cotton piece (15 mm×15 mm) absorbing each test solution was placed on each coating film for one hour. During the test, the wet state of the cotton piece was maintained. One hour after the placement, the cotton piece was removed, and the state of the coating film was evaluated by the score determined according to Table 2. Separately, when the coating film was completely dried after removal of the cotton piece, the appearance of the coating film was observed again, and the state was evaluated on the basis of the same score. The two scores were summed, and the coating film was finally evaluated by the summed score.

(Solvents Used)
Solvent 1: aqueous ammonia (1.4 mass %)
Solvent 2: ethanol (50 mass %)
Solvent 3: isopropyl alcohol (70 mass %)
Solvent 4: aqueous sodium hydroxide (1 mass %)
MEK: methyl ethyl ketone
Detergent 1: Windex (Glass cleaner, product of Johnson SC)
detergent 2: FORMULA 409 (Kitchen cleaner, product of The Clorox Company)

TABLE 2

| Items | Changes in appearance | Dissolution/change in touch | Permeation | Remarks |
|---|---|---|---|---|
| Specific changes | Turbid Surface roughness Cracks | Dissolution Soft | Swell Permeation | Total score 1 is given regardless of the total score, if any score 0 is assigned. |
| Scores (Additional convention) | None: 4 Peripheral discoloration (negligible): 3 Turbid (slight): 2 Turbid (considerable): 1 Foamed or Cracked: 0 | None: 4 Peripheral dissolution: 3 Soft: 2 Partial dissolution of film: 1 Dissolution to substrate: 0 | None: 2 Yes: 1 | |
| Remarks | | Test sample was slightly pressed with a pair of tweezers after removal of cotton piece. Softness was evaluated for the resultant scratch mark. | | |

TABLE 3

| | Scores | | | | | | | |
|---|---|---|---|---|---|---|---|---|
| | Solvent 1 | Solvent 2 | Solvent 3 | Solvent 4 | MEK | Water | Detergent 1 | Detergent 2 |
| Ex. 1 | 16 | 16 | 15 | 20 | 10 | 20 | 18 | 20 |
| Ex. 2 | 16 | 18 | 17 | 20 | 16 | 20 | 17 | 20 |
| Ex. 3 | 16 | 16 | 15 | 20 | 11 | 20 | 18 | 20 |
| Ex. 4 | 16 | 18 | 17 | 20 | 17 | 20 | 18 | 20 |
| Comp. Ex. 1 | 14 | 15 | 10 | 17 | 2 | 17 | 12 | 12 |
| Comp. Ex. 2 | 15 | 15 | 9 | 17 | 4 | 17 | 10 | 12 |
| Comp. Ex. 3 | 2 | 12 | 2 | 2 | 2 | 17 | 2 | 2 |

TABLE 4

| | Scores | | | | | | | |
|---|---|---|---|---|---|---|---|---|
| | Solvent 1 | Solvent 2 | Solvent 3 | Solvent 4 | MEK | Water | Detergent 1 | Detergent 2 |
| Ex. 5 | 20 | 20 | 18 | 19 | 20 | 20 | 20 | 20 |
| Ex. 6 | 20 | 18 | 18 | 20 | 20 | 20 | 20 | 20 |
| Ex. 7 | 20 | 20 | 18 | 20 | 20 | 20 | 20 | 20 |
| Ex. 8 | 20 | 20 | 18 | 20 | 20 | 20 | 20 | 20 |
| Comp. Ex. 4 | 18 | 18 | 17 | 2 | 20 | 20 | 16 | 16 |
| Comp. Ex. 5 | 18 | 15 | 16 | 5 | 18 | 20 | 16 | 18 |
| Comp. Ex. 6 | 18 | 14 | 14 | 2 | 18 | 20 | 14 | 18 |

As shown in Tables 3 and 4, the coating films formed in Examples 1 to 8 exhibited excellent solvent resistance, as compared with the coating films produced by use of the same aqueous resins in Comparative Examples 1 to 6.

Example 9

The carbodiimide solution produced in Synthesis Example 2 (2.0 g) was added to a polyurethane resin (U915, product of Alberdingk) (10 g), and the mixture was sufficiently stirred, to thereby prepare an aqueous coating composition.

The thus-prepared aqueous coating composition was cast on an ABS plate (200 mm×100 mm×1 mm) to a coating thickness of 20 μm, to thereby form a coating film. Then, the film was cured at 80° C. for 10 minutes.

Example 10

The procedure of Example 9 was repeated, except that the carbodiimide solution produced in Synthesis Example 3 was used instead of that produced in Synthesis Example 2, to thereby form a coating film.

Example 11

The procedure of Example 9 was repeated, except that the carbodiimide solution produced in Synthesis Example 4 was used instead of that produced in Synthesis Example 2, to thereby form a coating film.

Example 12

The procedure of Example 9 was repeated, except that the carbodiimide solution produced in Synthesis Example 5 was used instead of that produced in Synthesis Example 2, to thereby form a coating film.

Comparative Example 7

The procedure of Example 9 was repeated, except that the carbodiimide solution produced in Synthesis Example 6 (2.6 g) was used instead of that produced in Synthesis Example 2, to thereby form a coating film.

Comparative Example 8

The procedure of Example 9 was repeated, except that the carbodiimide solution produced in Synthesis Example 7 (2.0 g) was used instead of that produced in Synthesis Example 2, to thereby form a coating film.

Comparative Example 9

The procedure of Example 9 was repeated, except that a polyurethane resin (U915, product of Alberdingk) (10 g) was used without adding an carbodiimide solution, to thereby form a coating film.

The coating films produced in the Examples were subjected to the cross-cutting test in the following manner. Table 6 shows the results.

(Cross-Cutting Test)

In accordance with the cross-cutting method (JIS K-5600), each coating film was cut into a lattice (10×10, with a spacing of 1 mm), and the lattice was evaluated on the basis of the score table (Table 5).

TABLE 5

| Score | Peeling |
|---|---|
| 5B | no peel (0%) |
| 4B | ≤5% peeling |
| 3B | 5-15% peeling |
| 2B | 15-35% peeling |
| 1B | 35-65% peeling |
| 0B | ≥65% peeling |

TABLE 6

| | Score |
|---|---|
| Ex. 9 | 5B |
| Ex. 10 | 5B |
| Ex. 11 | 5B |
| Ex. 12 | 5B |
| Comp. Ex. 7 | 3B |
| Comp. Ex. 8 | 3B |
| Comp. Ex. 9 | 2B |

As shown in Table 6, the coating films formed in Examples 9 to 12 exhibited excellent adhesion, as compared with the coating films produced by use of the same aqueous resins in Comparative Examples 7 to 9.

Industrial Applicability

Aqueous resin compositions containing the carbodiimide compound or the carbodiimide composition of the present invention exhibit excellent water resistance, solvent resistance, adhesion, etc. Thus, such a resin composition is suitable for use as a paint, an ink, a fiber-treating agent, an adhesive, a coating agent, or the like.

The invention claimed is:

1. A carbodiimide compound represented by formula (1):

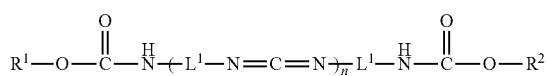

(1)

wherein $R^1$ represents a group represented by formula (a):

(a)

wherein $R^3$ represents a C1 to C3 alkyl group; and $R^4$ represents a hydrogen atom or a C1 to C3 alkyl group; $R^2$ represents a group represented by formula (a) or (b):

(b)

wherein $R^5$ represents a C1 to C4 alkyl group, $R^6$ represents a hydrogen atom or a methyl group; and m is an integer of 4 to 30; n is an integer of 1 to 15; $L^1$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^1$s may be identical to or different from one another).

2. A carbodiimide compound represented by formula (1-a):

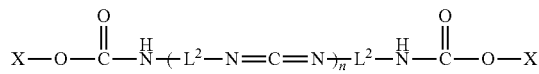
(1-a)

wherein X represents a group represented by formula (a):

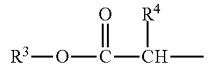
(a)

wherein $R^3$ represents a C1 to C3 alkyl group; and $R^4$ represents a hydrogen atom or a C1 to C3 alkyl group, and a plurality of Xs may be identical to or different from one another; n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another.

3. A carbodiimide compound represented by formula (1-b):

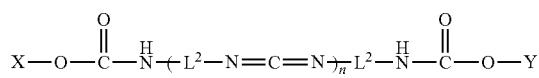
(1-b)

wherein X represents a group represented by formula (a):

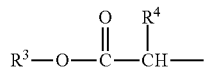
(a)

wherein $R^3$ represents a C1 to C3 alkyl group; and $R^4$ represents a hydrogen atom or a C1 to C3 alkyl group); Y represents a group represented by formula (b):

(b)

wherein $R^5$ represents a C1 to C4 alkyl group, $R^6$ represents a hydrogen atom or a methyl group; and m is an integer of 4 to 30; n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another.

4. A carbodiimide compound according to claim 1, wherein $R^3$ is a methyl group, and $R^4$ is a hydrogen atom or a methyl group.

5. An aqueous coating composition comprising a carbodiimide compound as recited in claim 1, and a cross-linkable aqueous resin.

6. A carbodiimide composition comprising a carbodiimide compound represented by formula (1-a); a carbodiimide compound represented by formula (1-b); and a carbodiimide compound represented by formula (2):

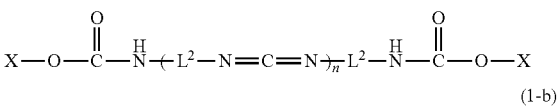
(1-a)

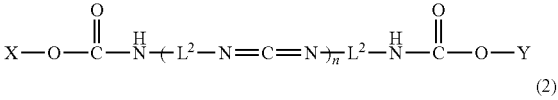
(1-b)

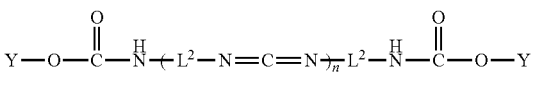
(2)

wherein X represents a group represented by formula (a):

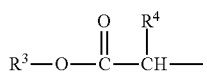
(a)

wherein $R^3$ represents a C1 to C3 alkyl group; and $R^4$ represents a hydrogen atom or a C1 to C3 alkyl group, and a plurality of Xs may be identical to or different from one another; Y represents a group represented by formula (b):

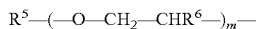
(b)

wherein $R^5$ represents a C1 to C4 alkyl group, $R^6$ represents a hydrogen atom or a methyl group; and m is an integer of 4 to 30, and a plurality of Ys may be identical to or different from one another; n is an integer of 1 to 15; $L^2$ represents a C1 to C18 divalent aliphatic hydrocarbon group, a C3 to C13 divalent alicyclic hydrocarbon group, a C6 to C14 divalent aromatic hydrocarbon group, or a C3 to C12 divalent heterocyclic group; and a plurality of $L^2$s may be identical to or different from one another.

7. A carbodiimide composition according to claim 6, wherein $R^3$ is a methyl group, and $R^4$ is a hydrogen atom or a methyl group.

8. A carbodiimide composition according to claim 6, which has a mole ratio of X to Y of 1:10 to 30:1.

9. An aqueous coating composition comprising a carbodiimide composition as recited in claim 6, and a cross-linkable aqueous resin.

10. An aqueous coating composition according to claim 9, wherein the cross-linkable aqueous resin is at least one species selected from among a water-soluble or water-dispersible urethane resin, acrylic resin, and polyester resin, each having a carboxyl group in a molecule thereof.

* * * * *